US011807817B2

(12) United States Patent
Senetar et al.

(10) Patent No.: US 11,807,817 B2
(45) Date of Patent: Nov. 7, 2023

(54) PROCESS FOR RECYCLING SUPPLEMENTAL FUEL FOR REGENERATING CATALYST

(71) Applicant: UOP LLC, Des Plaines, IL (US)

(72) Inventors: John J. Senetar, Naperville, IL (US); Joseph A. Montalbano, Elmhurst, IL (US); Nasim Ghazinoor, Hoffman Estates, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/314,286

(22) Filed: May 7, 2021

(65) Prior Publication Data

US 2022/0333018 A1  Oct. 20, 2022

Related U.S. Application Data

(60) Provisional application No. 63/023,506, filed on May 12, 2020.

(51) Int. Cl.
   *B01J 23/90* (2006.01)
   *B01J 29/90* (2006.01)
   *C10G 11/18* (2006.01)

(52) U.S. Cl.
   CPC .......... *C10G 11/182* (2013.01); *C10G 11/187* (2013.01); *C10G 2300/1081* (2013.01); *C10G 2300/4081* (2013.01)

(58) Field of Classification Search
   CPC ........ B01J 20/34; B01J 20/3433; B01J 21/20; B01J 23/92; B01J 23/94; B01J 23/96;
   (Continued)

(56) References Cited

U.S. PATENT DOCUMENTS 4,695,662 A * 9/1987 Vora ........................ C07C 41/06
                                                585/324
5,160,717 A   11/1992 Lok et al.
(Continued)

FOREIGN PATENT DOCUMENTS

KR  20190129298 A   11/2019
WO  WO2017058854 A1 †  4/2017
(Continued)

OTHER PUBLICATIONS

International Search Report and Written Opinion PCT/US 2021/031774 dated Aug. 26, 2021.

*Primary Examiner* — Youngsul Jeong
*Assistant Examiner* — Jason Y Chong
(74) *Attorney, Agent, or Firm* — Paschall & Associates LLC; James C. Paschall

(57) ABSTRACT

A composition of fuel gas that when mixed with spent catalyst and oxygen has an induction time that allows bubbles to break up while combusting in the regenerator. Bubble breakage in a dense bed avoids generation of a flame that can generate hot spots in the regenerator which can damage equipment and catalyst. The fuel gas can be obtained from paraffin dehydrogenation products, so it can sustain operation of the unit even in remote locations. Heavier streams can be mixed with lighter streams to obtain a fuel gas composition with a desirable induction time to avoid such hot spots. Mixing of a depropanizer bottom stream and/or deethanizer overhead stream with lighter gas streams such as cold box light gas or PSA tail gas can provide the desired fuel gas composition.

15 Claims, 4 Drawing Sheets

(58) Field of Classification Search
CPC ... B01J 38/02; B01J 38/04; B01J 38/10; B01J 38/12; B01J 38/14; B01J 38/18; B01J 38/20; C10G 11/182; C10G 11/187; C10G 2300/1081; C10G 2300/4081
See application file for complete search history.

(56) References Cited

U.S. PATENT DOCUMENTS

| | | |
|---|---|---|
| 10,227,271 B2 | 3/2019 | Pretz |
| 2011/0137101 A1* | 6/2011 | Myers ..................... B01J 23/94 |
| | | 502/56 |
| 2012/0312722 A1 | 12/2012 | Cammy et al. |
| 2013/0331586 A1* | 12/2013 | Dreyer .................... A23D 9/02 |
| | | 554/163 |
| 2016/0289144 A1* | 10/2016 | Pretz ....................... C07C 7/12 |

FOREIGN PATENT DOCUMENTS

| | | |
|---|---|---|
| WO | 2020061070 A1 | 3/2020 |
| WO | WO2020009860 A1 † | 9/2020 |

* cited by examiner
† cited by third party

PROCESS FOR RECYCLING SUPPLEMENTAL FUEL FOR REGENERATING CATALYST

CROSS-REFERENCE TO RELATED APPLICATIONS

This application claims priority from provisional application 63/023,506, filed May 12, 2020, incorporated herein in its entirety.

FIELD

The field is the regeneration of catalyst and particularly the combustion of coke from fluidized catalyst.

BACKGROUND

Light olefin production is vital to the production of sufficient plastics to meet worldwide demand. Paraffin dehydrogenation (PDH) is a process in which light paraffins such as ethane and propane can be dehydrogenated to make ethylene and propylene, respectively. Dehydrogenation is an endothermic reaction which requires external heat to drive the reaction to completion.

In PDH reactions with fluidized catalyst, coke can deposit on the catalyst while catalyzing the reaction. The catalyst may be regenerated in a catalyst regenerator by combusting coke from the catalyst in the presence of oxygen. The hot regenerated catalyst may then be transferred back to the reactor to catalyze the reaction. However, the coke produced in the PDH reaction can provide insufficient heat from combustion in the regenerator to promote the endothermic dehydrogenation process. Hence, supplemental fuel such as fuel gas may be fed to the catalyst regenerator to heat the catalyst sufficiently to transfer sufficient enthalpy to drive the endothermic reaction. Conversely, if insufficient heat is provided to drive the endothermic reaction, olefin production can suffer.

The regeneration process and equipment must be designed to minimize damage to the catalyst and to the regeneration equipment. This can be particularly challenging when fuel gas is added to the regenerator which can promote hot spots in areas where fuel gas combusts with insufficient means to disperse the heat. A high degree of vapor and catalyst mixing ensures complete combustion of the supplemental fuel gas and good heat transfer between vapor and catalyst. The catalyst is a large heat sink, so the supplemental fuel gas should be burned while in intimate contact with the dense catalyst phase to avoid excessively high dilute catalyst phase temperature. The catalyst density in the dense catalyst phase is at least 200 kg/m$^3$ (12.5 lb/ft$^3$), and the catalyst density in the dilute catalyst phase is no more than 100 kg/m$^3$ (6.3 lb/ft$^3$). Excess dilute catalyst phase temperatures can result in thermal damage to the surrounding catalyst and regeneration equipment because the heat is insufficiently dispersed in the absence of the dense catalyst phase. Afterburn of combustibles downstream of the dense catalyst phase or even downstream of the regenerator can cause further damage to equipment not rated for extremely high temperature.

Products from PDH include light gases, hydrogen and methane, unconverted ethane and propane, desired products, ethylene and propylene, and heavier hydrocarbon byproducts. Recovery systems are designed to recover the propylene and recycle propane to the PDH reactor. Use of the heavier hydrocarbons can often be uneconomical due to the expense of conversion to useful products or transport to conversion facilities.

There is a need, therefore, for improved fuel gas compositions and methods of recovering fuel gas for heating dehydrogenation catalyst in a catalyst regeneration process.

BRIEF SUMMARY

We have discovered a composition of fuel gas that when mixed with spent catalyst and oxygen has an induction time that allows bubbles to break up while combusting in the regenerator. Bubble breakage avoids generation of a flame that can generate hot spots in the regenerator which can damage equipment and catalyst. The fuel gas composition can be obtained from paraffin dehydrogenation products, so it can sustain operation of the unit even in remote locations. Heavier streams can be mixed with lighter streams to obtain a fuel gas with a desirable induction time. Mixing of a depropanizer bottom stream and/or deethanizer overhead stream with lighter gas streams such as cold box light gas or PSA tail gas can provide the desired fuel gas composition.

DEFINITIONS

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

The term "fuel gas" comprises hydrocarbons, hydrogen and mixtures thereof.

As used herein, the term "predominant" or "predominate" means greater than 50%, suitably greater than 75% and preferably greater than 90%.

The term "Cx" is to be understood to refer to molecules having the number of carbon atoms represented by the subscript "x". Similarly, the term "Cx−" refers to molecules that contain less than or equal to x and preferably x and less carbon atoms. The term "Cx+" refers to molecules with more than or equal to x and preferably x and more carbon atoms.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "a component-rich stream" means that the rich stream coming out of a vessel has a greater concentration of the component than the feed to the vessel.

As used herein, the term "a component-lean stream" means that the lean stream coming out of a vessel has a smaller concentration of the component than the feed to the vessel.

DETAILED DESCRIPTION

Figure 1:
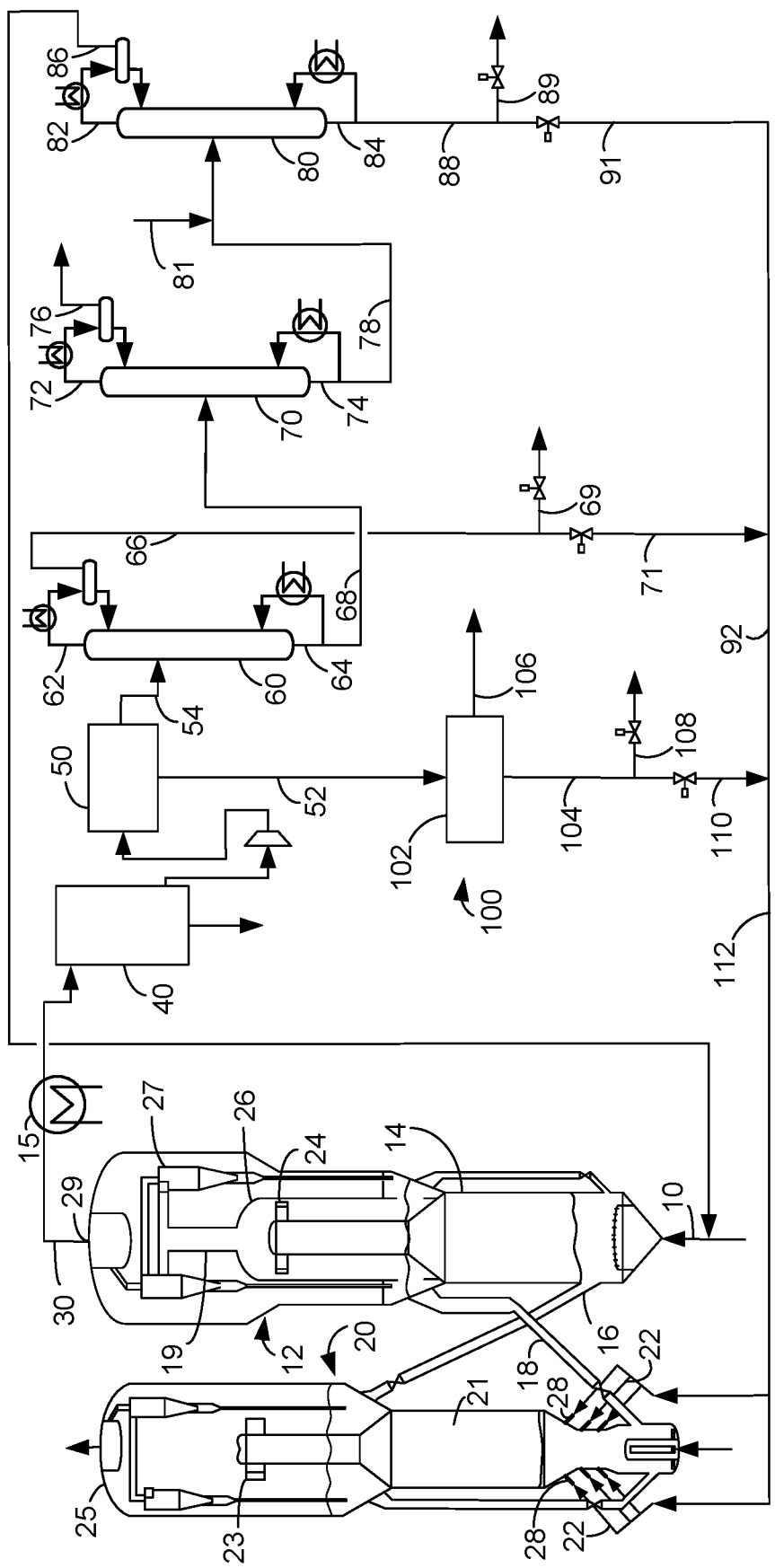
FIG. 1 is a schematic drawing of a process and apparatus of the present disclosure.

An exemplary PDH process is shown in FIG. 1. A reactant stream in line 10 concentrated in propane and/or perhaps isobutane or normal butane may be preheated and fed to a reactor 12. The reactant stream in some cases may include butane. In the reactor 12, the reactant stream may be fed to a riser 14 and reacted by contact with a stream of fluidized regenerated catalyst from a conduit 16. The reactant stream and the stream of fluidized catalyst both travel up the riser 14 while catalytically converting reactant paraffins to product olefins. An initial separation of product gases from catalyst may be performed by an initial separator 24 with tangential arms that transport catalyst and product gas tangentially in a cylindrical containment vessel 26. The swirling angular movement of the product gases and catalyst effect a separation of catalyst from product gas by centripetal acceleration. The separated catalyst loses momentum and falls downwardly into a bed of catalyst while separated product gases rise in the reactor 12. The initial separator may also be a ballistic-style separator. A gas recovery conduit 19 carries product gases upwardly to further separation from entrained catalyst in equipment such as cyclones 27. A vaporous reactor effluent stream comprising a light loading of residual catalyst and gaseous products is discharged from the reactor 12 through a reactor outlet 29 in line 30. Hot product gases may be quenched in the reactor 12 downstream of the initial separation of catalyst in the initial separator 24 such as in the gas recovery conduit 19.

The dehydrogenation catalyst may be of any of a variety of catalysts suitable for a fluidized dehydrogenation unit. The dehydrogenation catalyst selected should minimize cracking reactions and favor dehydrogenation reactions. Suitable catalysts for use herein include amorphous material or molecular sieves which may be dispersed in a porous inorganic carrier material such as silica, aluminum, zirconium, or clay. An exemplary embodiment of a catalyst includes crystalline silica-alumina or silica-alumina-phosphate as the primary active component, a matrix, a binder, and a filler.

The primary active component ranges from about 10 to about 50 weight percent of the catalyst and may have a lattice structure that limits the size range of hydrocarbon molecules that can enter the lattice. The molecular sieves appropriate for the primary active component should have medium and smaller average pore size. Typically, molecular sieves with medium and smaller average pore size have pores with openings of no more than 0.7 nm in effective diameter defined by rings of ten or fewer.

The matrix component may include amorphous alumina or silica, and the binder and filler provide physical strength and integrity. Silica sol or alumina sol may be used as the binder and kaolin clay may be used as the filler. The catalyst particles may have a nominal diameter of about 20 to about 150 micrometers with the average diameter of about 70 to about 90 micrometers.

The dehydrogenation catalyst may support a dehydrogenation metal. The dehydrogenation metal may be a one or a combination of transition metals. A noble metal may be a preferred dehydrogenation metal; however, a IIB or a IIIB metal may be a suitable dehydrogenation metal alone or in combination with other dehydrogenation metals. Iron, tungsten, gallium, copper, zinc or zirconium alone or in combination with each other or a noble metal may be suitable dehydrogenation metals. Combustion promoters may be utilized in addition to the catalyst. Metals may be incorporated into the lattice structure of the molecular sieve.

The acid function of the catalyst should be minimized to prevent cracking and favor dehydrogenation. Alkali metals and alkaline earth metals may be also be included in the catalyst to attenuate the acidity of the catalyst. Rare earth metals may be included in the catalyst to control the activity of the catalyst. Concentrations of 0.05 to 10 wt % metals may be incorporated into the catalyst. In the case of the noble metals, it is preferred to use about 0.05 to about 2 wt % noble metal.

The conditions in the dehydrogenation reaction may include a temperature of about 500 to about 800° C., a pressure of about 40 to about 310 kPa and a catalyst-to-oil ratio of about 5 to about 100. The dehydrogenation reaction may be conducted in a fluidized manner such that gas, which may be the reactant paraffins or an inert fluidizing gas, is distributed to the reactor in a way that lifts the dehydrogenation catalyst in the reactor vessel while catalyzing the dehydrogenation of propane, ethane and/or other hydrocarbons. During the catalytic dehydrogenation reaction, coke is deposited on the dehydrogenation catalyst so as to reduce the activity of the catalyst. The dehydrogenation catalyst must then be regenerated.

The spent dehydrogenation catalyst is transported by a conduit 18 to a regenerator 20 to combust the coke and regenerate the spent catalyst into regenerated catalyst. The catalyst regenerator 20 includes a combustion chamber 21 and a catalyst separator 23 which separates regenerated catalyst from flue gas generated in the combustion chamber 21 as it enters a separation chamber 25. An oxygen supply gas is provided to the combustion chamber 21 which lifts the spent catalyst in the combustion chamber 21 into the separation chamber 25. The coke is burned off the spent catalyst by contact with the oxygen supply gas at regeneration conditions. In an exemplary embodiment, air is used as the oxygen supply gas, because air is readily available and provides sufficient oxygen for combustion. About 10 to about 15 kg of air are required per kg of coke burned off of the spent catalyst. Exemplary regeneration conditions include a temperature from about 500° C. (900° F.) to about 900° C. (1700° F.) and a pressure of about 103 kPa (abs) (15 psia) to about 450 kPa (abs) (70 psia) in the regenerator 20. Regenerated catalyst is returned to the reactor 12 in the conduit 16. Fuel gas is added to the regenerator such as by lines 22 through respective fuel gas distributor nozzles 28 to boost the heat generated therein by combustion of the fuel gas in addition to combustion of the coke on the catalyst.

We have found it desirable to promote combustion of fuel gas and coke in the regenerator 20 in a way that avoids propagation of a flame. Addition of fuel gas to the regenerator is more susceptible to flame generation compared to catalyst regeneration without addition of fuel gas. Flames generate intense heat which is in excess of that necessary to regenerate and heat catalyst. Moreover, intense heat from a flame can damage catalyst and equipment. Propagation of a flame can be avoided by breaking up larger bubbles before the fuel gas ignites in the regenerator.

Figure 2:
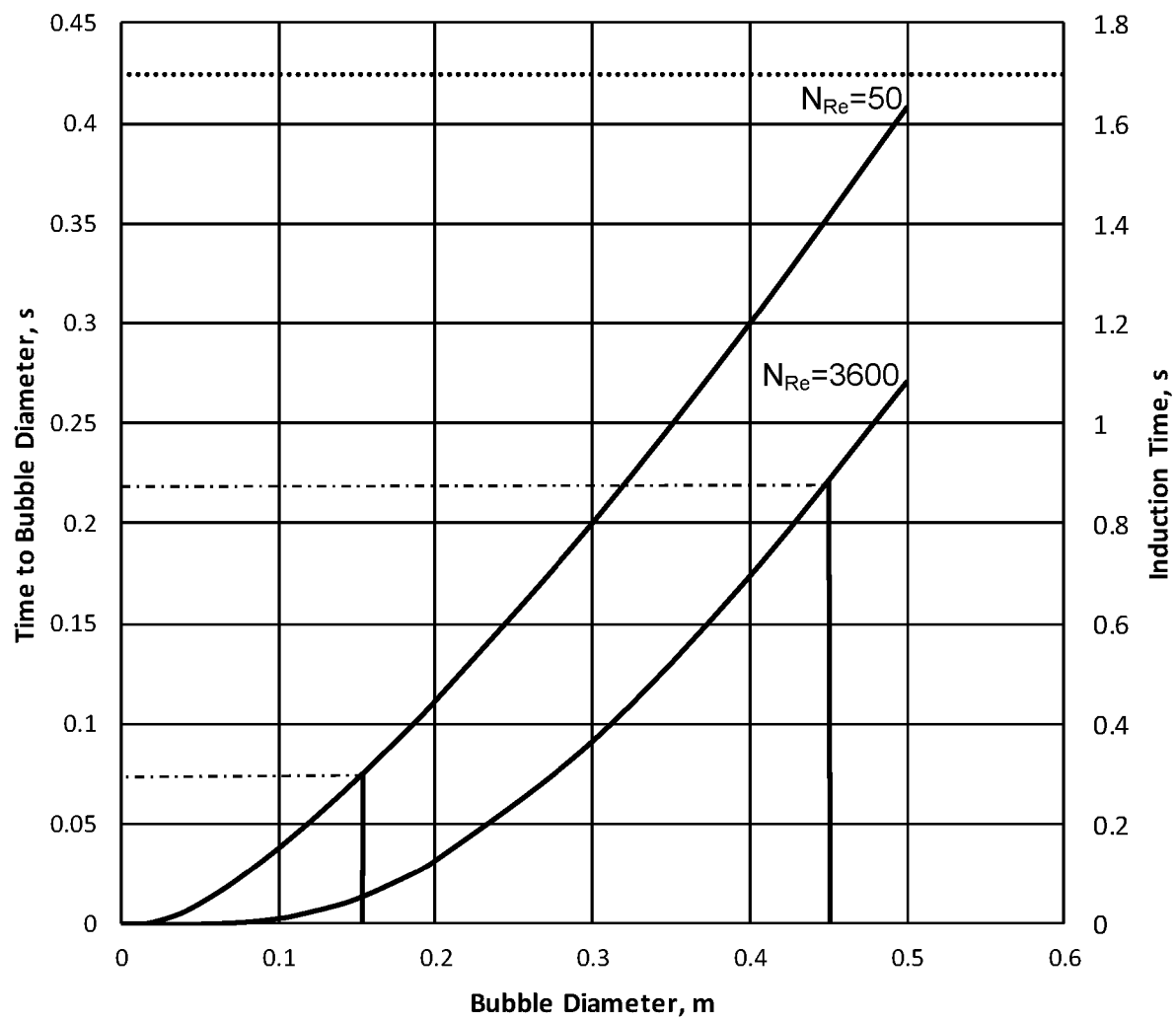
FIG. 2 is a plot of Time to Bubble Diameter and Induction Time vs. Bubble Diameter for a given Reynolds No.

FIG. 2 presents a plot of Time to Bubble Diameter and Induction Time vs. Bubble Diameter which follows a curve delineated by a particle Reynolds No. Two curves are depicted each of a particular Reynolds No., an upper curve at a Reynolds No. of 50 and a lower curve at a Reynolds No. of 3600. The left vertical axis is labeled with Time to Bubble Diameter, and the right vertical axis is labeled with Induction Time. The left vertical line in the plot at about 0.15 m represents a particular maximum stable bubble diameter at a particle Reynolds No. of 50, corresponding to the upper curve, for a fuel gas emitted from a jet of gas extending from the fuel distributor nozzle 28, shown in FIG. 1. The jet is the stream of gas contiguous with the fuel distributor nozzle 28. The dotted horizontal line from the intersection of the particular maximum stable bubble diameter and the curve for the particle Reynolds No. of 50 represents the time of about 0.08 seconds that it takes the fuel gas jet to grow to the maximum stable bubble diameter of 0.15 m at the particle Reynolds No. of 50. The right vertical line in the plot at about 0.45 m represents a particular maximum stable bubble diameter at a particle Reynolds No. of 3600, corresponding to the lower curve, for a fuel gas emitted from the jet of gas extending from the fuel distributor nozzle 28. The dotted horizontal line from the intersection of the maximum stable bubble diameter and the curve for the particle Reynolds No. of 3600 represents the time of about 0.22 seconds that it takes the fuel gas jet to grow to the maximum stable bubble diameter of 0.45 m at the particle Reynolds No. of 3600.

The particle Reynolds No. is calculated according to Equation (1):

$$N_{Re,p} = \frac{(v_f \times D_p \times \rho_f)}{\mu_f} \quad (1)$$

wherein $N_{Re,p}$ is the particle Reynolds No., $v_f$ is the velocity of the fuel gas exiting the fuel distributor nozzle 28, $D_p$ is Sauter mean diameter of the catalyst particles, $\rho_f$ is the density of the fuel gas and $\mu_f$ is the dynamic viscosity of the fuel gas. The $N_{Re,p}$ should be between about 40 and about 4000 and preferably between about 50 and about 3600. The Reynolds Nos. in the plot in FIG. 2 is based on particle Reynolds No. If the Reynolds No. is based on the fluid, $N_{Re,f}$, $D_n$ representing the inner diameter of the fuel distributor nozzle 28 is substituted for $D_p$ in Equation (1) as shown in Equation (2):

$$N_{Re,f} = \frac{(v_f \times D_n \times \rho_f)}{\mu_f} \quad (2)$$

The selected $N_{Re,f}$ should be between about 10,000 and about 2,000,000.

Time to Bubble Diameter is calculated as the distance the bubble has traveled from the jet divided by the velocity of the bubble of a given diameter pursuant to V. Bejcek et al., BUBBLE SIZE ABOVE AN ISOLATED GAS JET PENETRATING A FLUIDIZED BED, Chem. Eng. Comm., vol. 62, 303-14 (1987), which is incorporated herein by reference.

The maximum stable bubble diameter, De max, is calculated from formula (3):

$$D_{emax} = 2\left[\frac{U_t^2}{g}\right] \quad (3)$$

wherein, $U_t$ is the terminal velocity of particles calculated for a particle that is 2.7 times the Sauter mean diameter, $D_p$, of the particles and g is the gravitational constant. Handbook of Powder Technology, GAS FLUIDIZATION, vol. 8, Mel Pell, Ed. (1990).

Bubbles that have not achieved the maximum stable bubble diameter and broken into smaller bubbles before the fuel gas induction time will ignite into a flame whose intense heat can damage equipment and catalyst. In calculations, we utilized an induction time from the GRI-MECH 3.0 Microkinetic Mechanism at http://combustion.berkeley.edu/gri-mech/.

In the example in FIG. 2, the induction time for oxidization of the fuel gas is 1.7 seconds which is significantly greater than the maximum time for stable bubble diameter of 0.27 seconds for a bubble diameter of 0.5 m and a particle Reynolds No. of 3600. A fuel gas with an induction time for oxidation of 1.7 seconds is even more significantly greater than the maximum time for stable bubble diameter of 0.08 seconds or for a bubble diameter of 0.15 and a particle Reynolds No. of 50. Bubbles that break up after exceeding the maximum stable bubble diameter will not typically produce a flame upon induction. The resulting smaller bubbles may also grow to the maximum stable bubble diameter before breaking up. A particle Reynolds No. should be selected that produces a bubble that achieves the maximum stable bubble diameter before reaching the induction time to avoid flame generation. A maximum stable bubble diameter should be between about 0.1 and about 0.5 meters, preferably between about 0.15 and 0.45 meters, and a time to maximum stable bubble diameter should be less than the induction time of the fuel gas added to the regenerator. A fuel gas composition may be selected that has an induction time that is no more than about 4 s, suitably no more than about 3 s, preferably no more than about 2 s, and more preferably no more than about 1.7 s. This will ensure that the fuel gas will combust at a desired location in the regenerator vessel 20 and not downstream of the regenerator vessel which can damage equipment Induction times of as low as about 0.05, about 0.1 or about 0.2 seconds may even be acceptable, so long the time to maximum stable bubble diameter is smaller.

Regenerator conditions will ensure that fuel gas combusts evenly without causing a flame which can damage the catalyst or equipment. Accordingly, a fuel gas composition should be selected with a sufficiently high induction time to allow fuel gas bubbles to reach their maximum stable bubble size to break up before the induction time has expired and ignition occurs, but not so high as to promote combustion downstream of the regenerator 20. Very short induction times such as less than 0.2 or 0.1 seconds are not suitable because they will combust before the bubble breaks up from its maximum size generating a flame and hot spots that can damage equipment. Long induction times such as over 4 seconds are not suitable because the risk increases that the fuel gas will not burn in the dense catalyst phase resulting in afterburn which can also damage regenerator or downstream equipment. A fuel gas composition that provides an induction time between 0.1 or 0.2 seconds and 4 seconds would be suitable for a paraffin dehydrogenation fluidized reactor 12.

Figure 3:
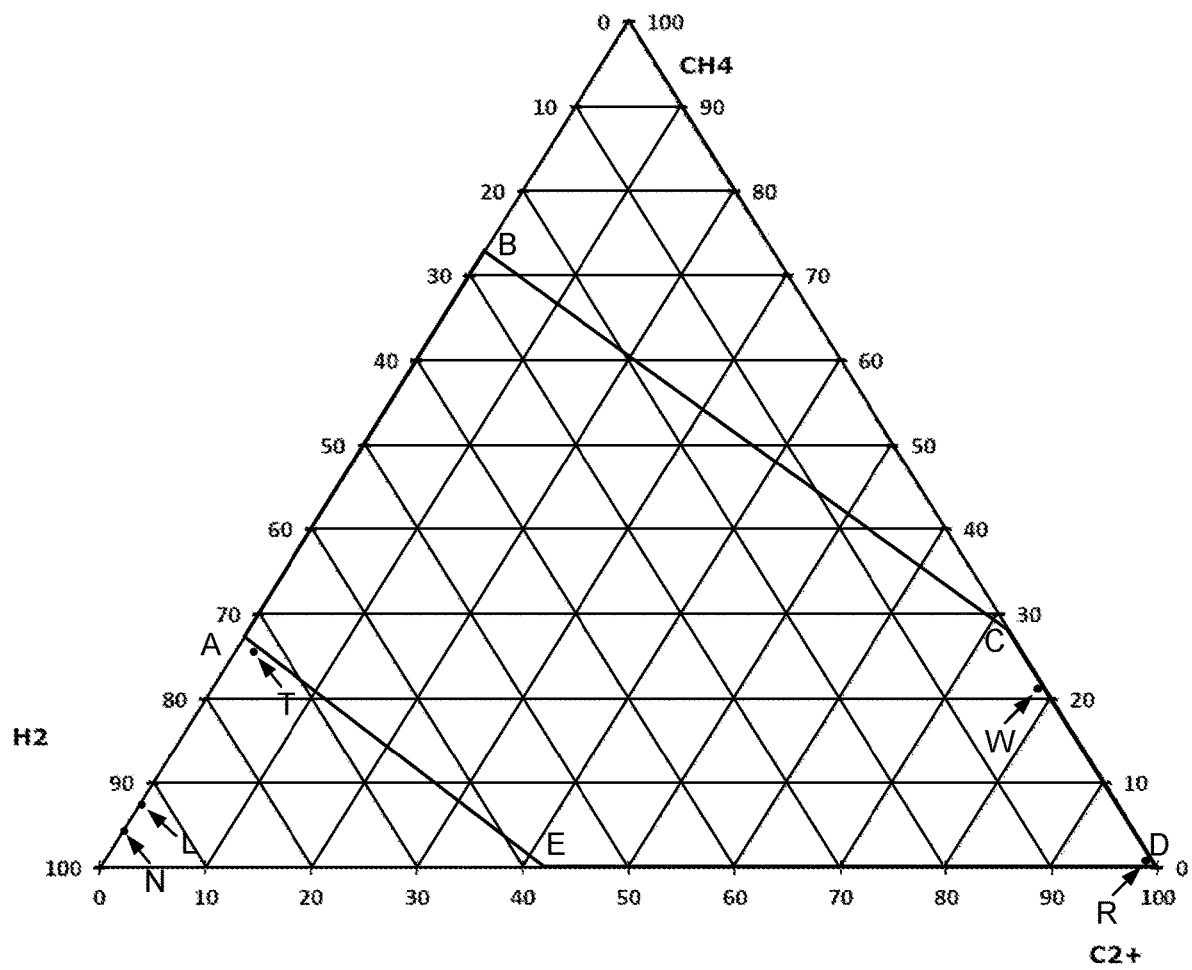
FIG. 3 is a ternary diagram of the present disclosure.

The ternary diagram in FIG. 3 represents fuel gas compositions with three combustible components. The three components are hydrogen, methane and C2+ hydrocarbons. The ternary diagram disregards non-combustibles such as trace impurities and moisture. The top vertex in the ternary diagram represents all methane. The bottom left vertex in the ternary diagram represents all hydrogen, and the bottom right vertex in the ternary diagram represents all C2+ hydrocarbons. We have found that a fuel gas that provides an induction time between about 0.1 and 4 seconds would provide suitable time to allow fuel gas bubbles to achieve their maximum stable bubble diameter before induction. The side BC of the pentagon superimposed on the ternary diagram of FIG. 3 represents a 4 second induction time. The side AE of the pentagon superimposed on the ternary diagram of FIG. 3 represents a 0.1 second induction time.

A suitable fuel gas composition should have specified mole fractions of hydrogen, methane, and C2+ hydrocarbons that are within the pentagonal compositional area ABCDE defined by vertices A, B, C, D and E in the ternary diagram of FIG. 3. The ternary diagram shows that net gas whose composition is indicated at point N falls far outside the preferred range for induction time. The high hydrogen content of net gas is expected to ignite extremely rapidly forming hot spots in the fluidized bed near the nozzle 28 from which fuel gas is injected. The light gas representing all of the product hydrogen and methane whose composition is indicated by point L on the diagram also falls far outside the preferred range of induction time due to its high hydrogen content. Similarly, but to a lesser extent, the ternary diagram shows that PSA tail gas whose composition is indicated by point T is also is expected to combust too rapidly at just below 0.1 seconds of induction time and falls outside the preferred range of induction time. The hydrogen content of the PSA tail gas may vary depending on the composition of net gas and the PSA separation efficiency.

A depropanizer bottoms stream composition is indicated by point R on the ternary diagram, and a deethanizer overhead stream composition is indicated by point W on the diagram. Both the depropanizer bottoms stream and the deethanizer overhead stream are expected to fall in the preferred range of induction times in the regenerator.

Fuel gas compositions that have mole fractions bound by the pentagon ABCDE on the ternary diagram in FIG. 3 provide a suitable induction times to avoid flame generation in the regenerator 20 and downstream afterburn. Each of the vertices A, B, C, D and E are represented by the mole fractions given in Table 1.

TABLE 1

| Vertex | Mole Fraction, % | | |
| --- | --- | --- | --- |
| | Hydrogen | Methane | C2+ Hydrocarbons |
| A | 73 | 27 | 0 |
| B | 28 | 72 | 0 |
| C | 0 | 28 | 72 |
| D | 0 | 0 | 100 |
| E | 58 | 0 | 42 |

Figure 4:
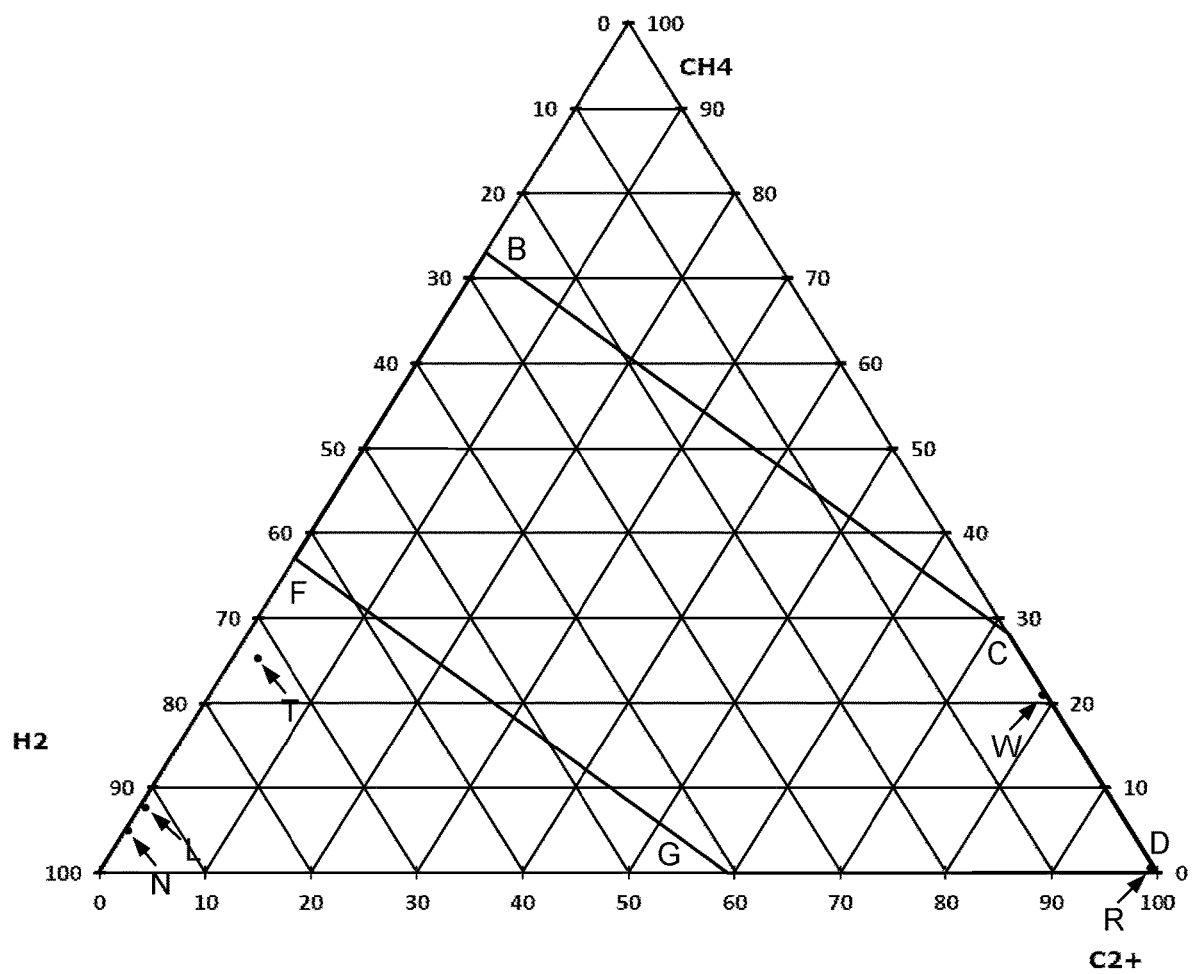
FIG. 4 is a ternary diagram of an alternative of the present disclosure.

It may be more preferred to utilize fuel gas compositions with an induction time of at least 0.2 seconds to ensure sufficient time to achieve maximum stable bubble diameter. The side FG of the pentagon superimposed on the ternary diagram of FIG. 4 represents 0.2 seconds of induction time. A preferred fuel gas composition is shown in FIG. 4 having specified mole fractions of hydrogen, methane, and C2+ hydrocarbons that are within the pentagonal compositional area FBCDG defined by vertices F, B, C, D and G in the ternary diagram of FIG. 4. Similar to the pentagonal area of FIG. 3, the net gas at point N, the light gas at point L, and the tail gas at point T all fall outside of the preferred pentagonal compositional area FBCDG. The deethanizer overhead stream represented by point W and the depropanizer bottoms stream represented by point R fall well within the preferred compositional area FBCDG. Fuel gas compositions that have mole fractions bound by the pentagon FBCDG on the ternary diagram in FIG. 4 provide preferred induction times that avoid flame generation in the regenerator 20 and beyond. Each of the vertices F, B, C, D and G are represented by the mole fractions given in Table 2.

TABLE 2

| Vertex | Mole Fraction, % | | |
| --- | --- | --- | --- |
| | Hydrogen | Methane | C2+ Hydrocarbons |
| F | 63 | 27 | 0 |
| B | 28 | 72 | 0 |
| C | 0 | 28 | 72 |
| D | 0 | 0 | 100 |
| G | 41 | 0 | 59 |

Additional preferences in fuel gas composition for catalyst regeneration in paraffin dehydrogenation will improve operation. Higher concentrations of heavier hydrocarbons in the fuel gas increase the induction time. Consequently, the fuel gas stream should comprise at least 10 mol % C2+ hydrocarbons, suitably at least 25 mol % C2+ hydrocarbons and preferably at least 40 mol % C2+ hydrocarbons to improve induction time.

The most desirable product of paraffin dehydrogenation is propylene, and thus the most desirable reagent is propane. Accordingly, the fuel gas stream should be prepared to have no more than 5 mol % and preferably no more than 1 mol % C3 hydrocarbons. C4+ hydrocarbons are not as valuable as the C3 hydrocarbons. Hence, when the C2+ hydrocarbon component is prepared for the ternary mixture by the removal of C3 hydrocarbons, the concentration of C4+ hydrocarbons will increase. The fuel gas composition preferably has at least 5 mol % C4+ hydrocarbons. The C2+ hydrocarbon component may comprise at least about 80 mol % C4+ hydrocarbons.

In the event that a butene product is a desired product from the reaction, the C2+ hydrocarbon component may comprise less than 10 mol %, suitably less than 5 mol % and preferably less than 1 mol % butane.

Hydrogen has the smallest induction time and is a valuable gas. Hence, the fuel gas stream should minimize the concentration of hydrogen and replace it with the least valuable other component in the ternary mixture which is methane. The fuel gas stream should then have at least 10 mol % methane and preferably at least 20 mol % methane. A ternary diagram such as shown in FIGS. 3 and 4 can be programmed into a controller to set the desired fuel gas mixture supplied to the regenerator based on compositions of the available fuel streams. Alternatively, or additionally, temperature sensors in the regenerator can provide a feedback signal to adjust the fuel composition based on temperature.

A process has been discovered for generating a fuel gas with the desired composition from vaporous reactor effluent stream discharged from a fluidized paraffin dehydrogenation reactor 12.

Turning back to FIG. 1, the vaporous reactor effluent stream in line 30 comprises light hydrocarbon and heavy hydrocarbon products and entrained catalyst. The catalyst is predominantly catalyst fines which have a largest diameter of no more than 40μ and preferably no more than 20μ. The vaporous reactor effluent stream may be cooled in cooler 15 such as an effluent cooler and fed to a contaminant removal unit 40 for removal of catalyst fines, water, acid gases and chlorides such as by use of a contact cooler, acid gas absorption, water washing and drying. The contaminant removal unit 40 may also be equipped to remove heavy hydrocarbons from the reactor effluent stream in line 30. A compressed, purified reactor effluent stream is then compressed in one or two stages and fed to a cold box 50.

The cold box 50 typically has a series of cryogenic heat exchangers between process and/or refrigerant streams and the compressed, purified reactor effluent stream followed by separators to remove vapor streams from liquid streams. Most of the hydrogen is recovered as a product gas stream in a product gas line 52 from the cold box 50. The concentration of hydrogen in the product gas stream increases proportionally to the flow rate of hydrogen that is recycled to the reactor 12. Methane and C2+ hydrocarbon concentration of the product gas stream will vary depending on the design and operation of the cold box 50. The product gas will be rich in hydrogen typically comprising at least 85 mol %, preferably at least 90 mol % hydrogen, about 1 to about 8 mol %, preferably about 5 mol %, methane and the balance C2+ hydrocarbons and nitrogen. A product liquid stream rich in methane and C2+ hydrocarbons is removed from the cold box in a product liquid line 54.

The product gas stream comprises excessive hydrogen to be burned as fuel gas in the regenerator 20. The hydrogen is too useful and it combusts too quickly in the regenerator 20. Hence, it is proposed to remove the hydrogen in a hydrogen removal unit 100. The hydrogen removal unit 100 may comprise a pressure swing adsorption unit 102 although a membrane unit is also contemplated. In the pressure swing adsorption unit 102, the product gas stream may be separated into a hydrogen rich stream and a methane rich stream which may be used to supplement the fuel gas stream.

In the hydrogen recovery unit 100, the net light product gas stream may be fed to the PSA unit 102 in which hydrogen is adsorbed onto an adsorbent in a plurality of beds in series while allowing larger molecules such as methane and C2+ hydrocarbons to pass by the adsorbent in the beds. The adsorption pressure may be about 1 MPa (150 psia) to about 1.7 MPa (250 psia) to adsorb hydrogen. A tail gas stream rich in methane and C2+ hydrocarbons exit the PSA unit 102 in a tail gas line 104. The adsorbent beds may be connected in series to cycle between pressures. Flow to each adsorbent bed is periodically terminated and the pressure in the terminated bed is decreased in stages to release void space gas and then to blow down to desorb hydrogen from the adsorbent in the terminated bed and pass into a hydrogen product stream in a hydrogen product line 106. A blow down pressure of 34.5 kPa (5 psia) to about 172 kPa (25 psia) may be used to desorb hydrogen from the adsorbent. A suitable adsorbent may be activated calcium zeolite A. The tail gas stream in the tail gas line 104 may comprise about 60 to about 85 mol % hydrogen, about 15 to about 35 mol % methane, preferably about 20 to about 30 mol % methane, and about 1 to about 10 mol % C2+ hydrocarbons, preferably about 2 to about 6 mol % C2+ hydrocarbons. A portion of the tail gas stream may be split between a product tail gas stream in line 108, which may be exported, and a tail fuel gas stream in line 110.

A deethanizer column 60 can separate the product liquid stream in line 54 into an ethane rich stream and a C3+ hydrocarbon rich stream. The deethanizer column 60 is operated to separate two fractions, the C2− hydrocarbon, ethane rich stream in a deethanizer overhead line 62 and a C3+ hydrocarbon rich stream in a deethanized bottoms line 64. The deethanizer overhead stream is withdrawn from an overhead of the deethanizer column 60 in the overhead line 62, condensed in a cooler and fed to a separator. A condensed deethanizer overhead stream is recycled to the deethanizer column 60 as reflux through a reflux line and the remaining uncondensed deethanizer overhead stream is withdrawn through a net deethanizer overhead stream in line 66. The ethane rich, deethanizer overhead stream will be highly concentrated in C2 hydrocarbons because much of the hydrogen and methane have been previously removed in the cold box 50. The deethanized C3+ hydrocarbon rich stream is withdrawn from the deethanizer column 60 through a deethanized bottoms line 64 from which a portion of the bottoms flows through a reboiler line and a reboiler heater and returns heated to the deethanizer column 60. The remaining portion of the deethanized C3+ hydrocarbon rich stream flows through the net deethanized bottoms line 68 and is fed to a C3 splitter column 70. The net deethanizer overhead stream in the net deethanizer overhead line 66 is rich in C2− hydrocarbons comprising about 50 to about 90 mol % C2 hydrocarbons and about 10 to about 50 mol % methane, suitably at least about 15 mol % methane, with the balance of usually no more than about 1 mol % hydrogen. A portion of the ethane rich, net deethanizer overhead stream may be split between a C2− hydrocarbon product stream in a C2 export line 69, that may be processed for recovery of ethylene product, and a C2− hydrocarbon fuel gas stream in line 71. Accordingly, the ethane rich, C2− hydrocarbon product stream may comprise at least 40 mol % and preferably at least about 70 mol % C2+ hydrocarbons. The deethanizer column 60 may operate with a bottoms temperature between about 70° C. (158° F.) and about 200° C. (392° F.) and an overhead pressure of about 1 MPa (gauge) (150 psig) to about 3 MPa (gauge) (435 psig).

The deethanized C3+ hydrocarbon rich stream may be further processed in a C3 splitter column 70 to recover a propylene rich product stream in a C3 splitter overhead line 72 and a propylene lean, C3+ hydrocarbon rich stream in a C3 splitter bottoms line 74. The C3 splitter overhead stream is withdrawn from an overhead of the C3 splitter column 70 in the overhead line 72, condensed in a cooler and fed to a separator. A condensed C3 splitter overhead stream is recycled to the C3 splitter column 70 as reflux through a reflux line and the remaining uncondensed C3 splitter overhead stream is withdrawn through a net C3 splitter overhead line 76 and recovered as propylene product. The C3 splitter overhead stream will be highly concentrated in propylene because most of the hydrogen, methane and C2 hydrocarbons were removed previously in the cold box 50 and the deethanizer column. The C3+ hydrocarbon rich stream is withdrawn from the C3 splitter column 70 through a C3 splitter bottoms line 74 from which a portion of the bottoms flows through a reboiler line and a reboiler heater and returns heated to the C3 splitter column 70. The remaining portion of the C3+ hydrocarbon rich reactor effluent stream flows through the net C3 splitter bottoms line 78 and is fed to a depropanizer column 80. The C3 splitter column 70 may operate at an overhead pressure of about 400 to about 2500 kPa (gauge), preferably about 500 to about 1000 kPa (gauge) and a bottoms temperature of about 0° C., preferably about 20° C., to about 50° C.

A depropanizer column 80 separates the C3+ hydrocarbon rich stream into a propane rich stream and a C4+ hydrocarbon rich stream from which said fuel gas stream can be taken. A heavy byproduct stream of C4+ hydrocarbons can be removed from the unconverted propane rich reactor effluent stream in a depropanizer column 80 to permit the unreacted propane to be recycled to the reactor 12. The C3+ hydrocarbon rich stream in the net C3 splitter bottoms line 78 may be further processed in the depropanizer column 80 to recover an unconverted propane rich stream in the overhead and a C4+ hydrocarbon rich stream in the bottoms. A fresh propane feed stream in a propane feed line 81 may also be processed in the depropanizer column 80 to remove heavier hydrocarbons than propane before feeding it to the reactor 12. The depropanizer column 80 is operated to separate two fractions, a propane rich stream in a depropanizer overhead line 82 and a C4+ hydrocarbon rich stream in a depropanizer bottoms line 84. The depropanizer overhead stream is withdrawn from an overhead of the depropanizer column 80 in the overhead line 82, condensed in a cooler and fed to a separator. A condensed depropanizer overhead stream is refluxed to the depropanizer column 80 as reflux through a reflux line and the remaining uncondensed depropanizer overhead stream is withdrawn through a net depropanizer overhead line 86 and transported to the reactor 12. The depropanizer overhead stream will be highly concentrated in propane because most of the hydrogen, methane, C2 hydrocarbons and propylene were removed previously in the cold box 50, the deethanizer column 60 and the C3 splitter column 70. The C4+ hydrocarbon rich stream is withdrawn from the depropanizer column 80 through a depropanizer bottoms line 84 from which a portion of the bottoms flows through a reboiler line and a reboiler heater and returns heated to the depropanizer column 80. The remaining portion of the C4+ hydrocarbon rich stream in the depropanizer bottoms line 88 comprises at least 40 mol % C2+ hydrocarbons and preferably about 100% C2+ hydrocarbons and at least about 70 mol % C4+ hydrocarbons. A portion of the C4+ hydrocarbon rich stream may be split between a C4+ hydrocarbon product stream in an export line 89 and a C4+ hydrocarbon fuel gas stream in line 91 having the same compositions as in line 88. The C4+ hydrocarbon also may be considered a C2+ hydrocarbon stream because it comprises hydrocarbons with greater than two carbon atoms. The depropanizer column 80 may operate at an overhead pressure of about 1000 to about 2000 kPa (gauge) and a bottoms temperature of about 70° C., preferably about 80° C., to about 150° C.

The sequence of the separation steps may be varied. Also, other recovery schemes may be employed and may include absorption, cryogenic distillation, membrane separation, and adsorption.

The C4+ hydrocarbon fuel gas stream in line 91 taken from the depropanizer bottoms stream in the depropanizer bottoms line 88 not exported as the hydrocarbon product stream in C4+ export line through an open control valve on line 91 may be mixed with the C2− hydrocarbon fuel gas stream in line 71 taken from the net deethanizer overhead stream in the deethanizer overhead line 66 not exported in the C2 export line 69 through an open control valve on line 71 to provide a mixed C2+ hydrocarbon fuel gas stream in a mixed fuel gas line 92. The mixed fuel gas stream in line 92 comprises at least 40 mol % C2+ hydrocarbons and at least 10 mol % methane and suitably at least about 70 mol % C2+ hydrocarbons and at least about 15 mol % methane. The mixed fuel gas stream may have at least about 20 mol % C4+ hydrocarbons.

In the event that butene is the product of the dehydrogenation reaction in the reactor 12 instead of propylene, the deethanizer column 60 may be replaced with a depropanizer column, the C3 splitter column 70 may be replaced with a C4 splitter column and the depropanizer column 80 may be replaced with a debutanizer column with other lines to and from the columns 60, 70 and 80 being essential the same as described. The debutanizer column overhead would recycle isobutane or normal butane to the reactor 12 in line 86 and isobutene or normal butene would be recovered from the process in a net C4 splitter overhead line 76. In this embodiment, the mixed fuel gas stream in line 92 may comprise more of the C3− hydrocarbon fuel gas stream from line 91 than the C5+ hydrocarbon fuel gas stream from line 91 and may comprise as much as all C3− hydrocarbon fuel gas stream from line 71. In the event that butene product is the desired product of the reaction, the mixed C2+ hydrocarbon fuel gas stream may comprise less than 10 mol %, suitably less than 5 mol % and preferably less than 1 mol % butane.

The tail fuel gas stream in line 110 not taken as the product tail gas stream in line 108 through a control valve on line 110 may be combined with the mixed fuel gas stream in line 92 to provide a combined fuel gas stream in a recycle line 112.

The recycle line 112 may combine the C4+ hydrocarbon fuel gas stream in line 91 taken from the depropanizer bottoms stream in the depropanizer bottoms line 88 not exported as the hydrocarbon product stream in C4+ export line 89; the C2− hydrocarbon fuel gas stream taken from the net deethanizer overhead stream in the deethanizer overhead line 66 not exported in the C2 export line 69; and the tail fuel gas stream in line 110 not taken as the product tail gas stream in line 108. Proportions of the C4+ hydrocarbon fuel gas stream from the depropanizer bottoms stream, the C2− hydrocarbon fuel gas stream from the deethanizer overhead and the tail fuel gas stream in the recycle line 112 can be respectively regulated by the product flow rates taken in lines 89, 69 and 108 governed by the control valves thereon and/or by control valves on lines 71, 91 and 110. The fuel gas in the recycle line 112 can be recycled to the regenerator 20 to be added to the regenerator 20 through lines 22 through respective fuel gas distributor nozzles 28. Combining portions of the depropanizer bottoms stream, the deethanizer overhead stream and the PSA tail gas stream in appropriate proportions will enable distribution of a fuel gas stream that exhibits desirable combustion properties in the regenerator 20 to combust coke deposits from the spent dehydrogenation catalyst stream when contacted with the oxygen supply gas stream. The combustion can generate sufficient heat on catalyst that can be transferred to supply requisite heat to the endothermic reaction in the reactor 12. The export lines 69, 89 and 106 can be exported separately or together to other locations or uses.

The disclosure provides a process that can recover byproduct components and unreacted C3 hydrocarbons from a paraffin dehydrogenation reaction and recycle byproduct components as fuel gas to the regenerator for heat supplementation. Unreacted C3 hydrocarbons can be recycled to the reactor. Lighter gas components that would not have desirable combustion properties can be mixed with heavier byproduct components to have appropriate combustion properties in the catalyst regenerator 20.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for regenerating catalyst from a catalytic reaction comprising providing a spent catalyst stream; distributing an oxygen supply gas stream to the spent catalyst stream; distributing a fuel gas stream to the spent catalyst stream; and combusting the fuel gas stream and carbon on the spent catalyst with the oxygen supply gas to provide flue gas and regenerated catalyst; wherein the fuel gas stream has respective mole fractions of methane, hydrogen and C2+ hydrocarbons bounded by a pentagonal compositional area ABCDE in FIG. 3. An embodiment of the disclosure is one, any or all of prior embodiments in this paragraph up through the first embodiment in this paragraph wherein the fuel gas stream has respective mole fractions of methane, hydrogen and C2+ hydrocarbons bounded by a pentagonal compositional area FBCDG on the ternary diagram in FIG. 4. An embodiment of the disclosure is one, any or all of prior embodiments in this paragraph up through the first embodiment in this paragraph wherein the fuel gas stream comprises at least 10 mol % C2+ hydrocarbons. An embodiment of the disclosure is one, any or all of prior embodiments in this paragraph up through the first embodiment in this paragraph wherein the fuel gas stream comprises at least about 40 mol % C2+ hydrocarbons. An embodiment of the disclosure is one, any or all of prior embodiments in this paragraph up through the first embodiment in this paragraph wherein the fuel gas stream comprises no more than 5 mol % C3 hydrocarbons. An embodiment of the disclosure is one, any or all of prior embodiments in this paragraph up through the first embodiment in this paragraph wherein the fuel gas stream comprises at least 5 mol % C4+ hydrocarbons. An embodiment of the disclosure is one, any or all of prior embodiments in this paragraph up through the first embodiment in this paragraph further comprising mixing together a first stream comprising at least about 40 mol % C2+ hydrocarbons and a second stream comprising at least about 15 mol % hydrogen and at least about 20 mol % methane to provide the fuel gas stream. An embodiment of the disclosure is one, any or all of prior embodiments in this paragraph up through the first embodiment in this paragraph wherein the first stream comprises at least about 15 mol % methane. An embodiment of the disclosure is one, any or all of prior embodiments in this paragraph up through the first embodiment in this paragraph further comprising mixing together a tail gas stream and a deethanizer overhead stream and/or a depropanizer bottoms stream.

A second embodiment of the disclosure is a process for producing a product from a catalytic reaction comprising reacting feed over a catalyst to produce a product stream and spent catalyst stream; separating the product stream into a product liquid stream and a product gas stream; separating a fuel gas stream from the product liquid stream; distributing the fuel gas stream and an oxygen supply gas stream to the spent catalyst stream; and combusting the fuel gas stream and the oxygen supply gas stream in the presence of the spent catalyst stream. An embodiment of the disclosure is one, any or all of prior embodiments in this paragraph up through the second embodiment in this paragraph wherein the first separating step comprises separating a hydrogen rich stream as the fuel gas stream from a methane rich stream as the product liquid stream. An embodiment of the disclosure is one, any or all of prior embodiments in this paragraph up through the second embodiment in this paragraph wherein the second separating step further comprises separating a propane rich stream from a C2+ hydrocarbon stream and providing the fuel gas stream from the C2+ hydrocarbon stream. An embodiment of the disclosure is one, any or all of prior embodiments in this paragraph up through the second embodiment in this paragraph further comprising recycling the propane rich stream to the reacting step. An embodiment of the disclosure is one, any or all of prior embodiments in this paragraph up through the second embodiment in this paragraph wherein the second separating step further comprises separating the methane rich stream into an ethane rich stream and a C3+ hydrocarbon rich stream and providing the fuel gas stream from the ethane rich stream. An embodiment of the disclosure is one, any or all of prior embodiments in this paragraph up through the second embodiment in this paragraph further comprising separating the C3+ hydrocarbon rich stream into a propylene rich stream and a propylene lean, C3+ hydrocarbon rich stream. An embodiment of the disclosure is one, any or all of prior embodiments in this paragraph up through the second embodiment in this paragraph further comprising separating the C3+ hydrocarbon rich stream into a propane rich stream and a C4+ hydrocarbon rich stream and providing the fuel gas stream from the C4+ hydrocarbon rich stream. An embodiment of the disclosure is one, any or all of prior embodiments in this paragraph up through the second embodiment in this paragraph further comprising separating the product gas stream into a hydrogen rich stream and a methane rich stream and supplementing the combustible gas stream with the methane rich stream.

A third embodiment of the disclosure is a process for producing a product from a catalytic reaction comprising reacting feed over a catalyst to produce a product stream and spent catalyst stream; separating a first portion of the product stream into an ethane rich stream and an ethane lean stream; separating a second portion of the product stream into a propane rich stream and a propane lean stream; taking one or both of the propane lean stream and the ethane rich stream as a combustible gas stream; distributing the combustible gas stream and an oxygen supply gas stream to the spent catalyst stream; and combusting the combustible gas stream and the oxygen supply gas stream in the presence of the spent catalyst stream. An embodiment of the disclosure is one, any or all of prior embodiments in this paragraph up through the third embodiment in this paragraph wherein the second portion of the product stream is taken from the ethane lean stream. An embodiment of the disclosure is one, any or all of prior embodiments in this paragraph up through the third embodiment in this paragraph further comprising separating the product stream into a product liquid stream and a product gas stream and the first portion and the second portion of the product stream are taken from the product liquid stream.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for regenerating catalyst from a catalytic reaction comprising:
providing a spent catalyst stream;
distributing an oxygen supply gas stream to said spent catalyst stream;
mixing together a first stream comprising at least about 40 mol % C2+ hydrocarbons and a second stream comprising at least about 15 mol % hydrogen and at least about 20 mol % methane to provide a fuel gas stream;
distributing said fuel gas stream to said spent catalyst stream; and
combusting said fuel gas stream and carbon on said spent catalyst with the oxygen supply gas stream to provide flue gas and regenerated catalyst; wherein said fuel gas stream has respective mole fractions of methane, hydrogen and C2+ hydrocarbons bounded by a pentagonal compositional area ABODE on a ternary diagram having a vertex A at 73 mol % hydrogen, 27 mol % methane and 0 mol % C2+ hydrocarbons; vertex B at 28 mol % hydrogen, 72 mol % methane and 0 mol % C2+ hydrocarbons; vertex C at 0 mol % hydrogen, 28 mol % methane and 72 mol % C2+ hydrocarbons; vertex D at 0 mol % hydrogen, 0 mol % methane and 100 mol % C2+ hydrocarbons; and vertex E at 58 mol % hydrogen, 0 mol % methane and 42 mol % C2+ hydrocarbons,
wherein said fuel gas provides an induction time between about 0.1 and 4 seconds.

2. The process of claim 1 wherein said fuel gas stream has respective mole fractions of methane, hydrogen and C2+ hydrocarbons bounded by a pentagonal compositional area FBCDG on the ternary diagram having a vertex F at 63 mol % hydrogen, 27 mol % methane and 0 mol % C2+ hydrocarbons; vertex B at 28 mol % hydrogen, 72 mol % methane and 0 mol % C2+ hydrocarbons; vertex C at 0 mol % hydrogen, 28 mol % methane and 72 mol % C2+ hydrocarbons; vertex D at 0 mol % hydrogen, 0 mol % methane and 100 mol % C2+ hydrocarbons; and vertex E at 41 mol % hydrogen, 0 mol % methane and 59 mol % C2+ hydrocarbons.

3. The process of claim 2 wherein said fuel gas stream comprises at least about 40 mol % C2+ hydrocarbons.

4. The process of claim 1 wherein said fuel gas stream comprises at least 10 mol % C2+ hydrocarbons.

5. The process of claim 1 wherein said fuel gas stream comprises no more than 5 mol % C3 hydrocarbons.

6. The process of claim 1 wherein said fuel gas stream comprises at least 5 mol % C4+ hydrocarbons.

7. The process of claim 1 wherein the first stream comprises at least about 15 mol % methane.

8. The process of claim 1 further comprising producing a product stream from the catalytic reaction;
separating said product stream into a product liquid stream and a product gas stream;
separating a tail gas stream from the product gas stream;
separating the product liquid stream in a deethanizer into an ethane rich stream and a C3+ hydrocarbon rich stream;
separating the C3+ hydrocarbon rich stream in a depropanizer into a propane rich stream and a C4+ hydrocarbon rich stream;
mixing together the tail gas stream and the deethanizer overhead stream and/or the depropanizer bottoms stream to form the fuel gas.

9. A process for producing a product from a catalytic reaction comprising:
reacting a feed over a catalyst to produce a product stream and a spent catalyst stream;
separating said product stream into a methane and C2+ hydrocarbons rich stream as a product liquid stream and a hydrogen rich stream as a product gas stream;
separating said product liquid stream into an ethane rich stream and a C3+ hydrocarbon rich stream;
separating said C3+ hydrocarbon rich stream into a propane rich stream and a C4+ hydrocarbon rich stream and providing a fuel gas stream from said C4+ hydrocarbon rich stream;
separating said product gas stream into a hydrogen rich stream and a methane rich stream;
supplementing said fuel gas stream with said methane rich stream;
distributing said fuel gas stream and an oxygen supply gas stream to said spent catalyst stream; and
combusting said fuel gas stream and said oxygen supply gas stream in the presence of said spent catalyst stream, wherein said fuel gas provides an induction time between about 0.1 and 4 seconds.

10. The process of claim 9 further comprising separating a propane rich stream from said methane and C2+ hydrocarbon stream and providing said fuel gas stream from said methane and C2+ hydrocarbon stream.

11. The process of claim 10 further comprising recycling said propane rich stream to said reacting step.

12. The process of claim 9 further comprising separating said C3+ hydrocarbon rich stream into a propylene rich stream and a propylene lean, C3+ hydrocarbon rich stream.

13. A process for producing a product from a catalytic reaction comprising:
reacting a feed over a catalyst to produce a product stream and a spent catalyst stream;
separating a first portion of said product stream into a hydrogen rich stream and a methane rich stream;
separating a second portion of said product stream into an ethane rich stream and an ethane lean stream;
separating a third portion of said product stream into a propane rich stream and a propane lean stream rich in C4+ hydrocarbons;
taking one or both of said propane lean stream and said ethane rich stream as a combustible gas stream;

distributing said combustible gas stream supplemented with said methane rich stream and an oxygen supply gas stream to said spent catalyst stream; and combusting said combustible gas stream and said oxygen supply gas stream in the presence of said spent catalyst stream, wherein said fuel gas provides an induction time between about 0.1 and 4 seconds.

14. The process of claim 13 wherein the second portion of said product stream is taken from said ethane lean stream.

15. The process of claim 13 further comprising separating said product stream into a product liquid stream and a product gas stream and the first portion and the second portion of said product stream are taken from said product liquid stream.

* * * * *